(12) United States Patent
Kim et al.

(10) Patent No.: US 9,341,590 B2
(45) Date of Patent: May 17, 2016

(54) COMPOSITE METAL OXIDE MATERIALS INCLUDING POLYCRYSTALLINE NANOFIBERS, MICROPARTICLES, AND NANOPARTICLES, GAS SENSORS USING THE SAME AS A SENSING MATERIAL THEREOF, AND MANUFACTURING METHODS THEREOF

(71) Applicant: Korea Advanced Institute of Science and Technology, Yuseong-gu, Daejeon (KR)

(72) Inventors: Il Doo Kim, Seoul (KR); Hee Jin Cho, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 44 days.

(21) Appl. No.: 14/570,644

(22) Filed: Dec. 15, 2014

(65) Prior Publication Data

US 2016/0041116 A1 Feb. 11, 2016

(30) Foreign Application Priority Data

Aug. 6, 2014 (KR) ........................ 10-2014-0101055

(51) Int. Cl.
| | |
|---|---|
| *G01N 30/02* | (2006.01) |
| *G01N 27/30* | (2006.01) |
| *D01D 5/00* | (2006.01) |
| *B05D 1/32* | (2006.01) |
| *B05D 1/00* | (2006.01) |
| *B05D 1/30* | (2006.01) |
| *B05D 1/02* | (2006.01) |
| *B05D 3/02* | (2006.01) |
| *C01G 19/02* | (2006.01) |
| *C01G 19/00* | (2006.01) |

(52) U.S. Cl.
CPC .............. *G01N 27/304* (2013.01); *B05D 1/005* (2013.01); *B05D 1/02* (2013.01); *B05D 1/30* (2013.01); *B05D 1/322* (2013.01); *B05D 3/0254* (2013.01); *C01G 19/00* (2013.01); *C01G 19/02* (2013.01); *D01D 5/003* (2013.01)

(58) Field of Classification Search
CPC ............ B05D 1/005; B05D 1/02; B05D 1/30; B05D 1/322; B05D 3/0254; C01G 19/00; C01G 19/02; D01D 5/003; G01N 27/304
See application file for complete search history.

(56) References Cited

U.S. PATENT DOCUMENTS

2012/0235094 A1\* 9/2012 Zhu .................... C01B 33/12
252/301.4 R

\* cited by examiner

*Primary Examiner* — Patrick Ryan
*Assistant Examiner* — Ben Lewis
(74) *Attorney, Agent, or Firm* — Fenwick & West LLP

(57) ABSTRACT

Provided are a composite metal oxide material, a method of manufacturing the same, and a gas sensor using the same as a sensing material thereof. The composite metal oxide material may include polycrystalline nanofibers and at least one of microparticles and nanoparticles. The use of the composite metal oxide material makes it possible to improve structural, mechanical, thermal, and lifetime stabilities of the gas sensor. Further, the presence of the microparticles and/or nanoparticles allows the gas sensor to have a base resistance lower than that of a nanofiber-based gas sensor. Since the microparticles and/or nanoparticles are attached to the nanofibers, the composite metal oxide material can have an increased mobility of electrons or holes and an increased surface area, and thus, the gas sensor can have fast response/recovery speeds and high gas sensitivity.

18 Claims, 14 Drawing Sheets

(500) Metal oxide nanofiber-nanoparticle-microparticle composite sensing material (100) Metal oxide nanoparticle (200) Metal oxide microparticle (300) Metal oxide nanofiber (400) Metal oxide nanoparticle aggregate (600) Metal oxide nanofiber-microparticle composite sensing material (200) Metal oxide microparticle (300) Metal oxide nanofiber

COMPOSITE METAL OXIDE MATERIALS INCLUDING POLYCRYSTALLINE NANOFIBERS, MICROPARTICLES, AND NANOPARTICLES, GAS SENSORS USING THE SAME AS A SENSING MATERIAL THEREOF, AND MANUFACTURING METHODS THEREOF

CROSS-REFERENCE TO RELATED APPLICATIONS

This U.S. non-provisional patent application claims priority under 35 U.S.C. §119 to Korean Patent Application No. 10-2014-0101055, filed on Aug. 6, 2014, in the Korean Intellectual Property Office, the entire contents of which are hereby incorporated by reference.

BACKGROUND

Example embodiments relate to a gas sensor, and in particular, to composite metal oxide materials including polycrystalline nanofibers, microparticles, and nanoparticles, gas sensors using the same as a sensing material thereof, and methods of manufacturing the same.

Recently, a gas sensor with extremely high sensitivity is being extensively studied to early detect harmful gases or exactly detect minute amounts of volatile organic compound gases contained in an exhalation of a human being. Currently, resistance-type gas sensors are commercialized, and most of them include a sensing material composed of micro-sized metal oxide particles, each of which has a diameter ranging from several hundreds of nanometers (nm) to several micrometers (μm).

An operation of such a resistance-type gas sensor is performed based on a modulation in thickness of an electron depletion layer, which is caused by oxygen adsorbed on a surface of a sensing material (e.g., metal oxide semiconductor). The thickness of the electron depletion layer can be changed by reaction with an oxidizing or reducing gas. For example, and thus, if a sensing material is exposed to a target gas, the thickness of the electron depletion layer is increased to have an increased resistance or is decreased to have a decreased resistance. Here, in the case where the sensing material is formed of relatively large particles with an average particle size of micrometer order, it is difficult to increase a surface area of the electron depletion layer formed on surfaces of the particles.

In the case of using nanoparticles, the electron depletion layer is formed on each of the nanoparticles, and this makes it possible to greatly increase a total surface area of the electron depletion layer constituting the sensing material. Accordingly, the thickness of the electron depletion layer formed on the surfaces of the nanoparticles can be largely changed by the reaction with an external gas, and this leads to a large change in resistance of the electron depletion layer and an increase in sensitivity of the gas sensor. In fact, several papers reported that the nanoparticle-based gas sensor can have very high sensitivity. However, most of currently-commercialized gas sensors are manufactured using a sensing material composed of particles with an average particle size of micrometer or sub micrometer order.

Long lifetime reliability is another important property for the gas sensor, but in the case where the sensing material is only formed of nanoparticles, there is a difficulty in achieving the long lifetime reliability property of the gas sensor. As an example, if the gas sensor is repeatedly used for a long period of time, accuracy thereof may be degraded. As another example, in the case that the gas sensor is exposed for a long period of time to an environment of high temperature of about 300° C.-400° C., which is within its normal operating temperature range thereof, the nanoparticles may be reacted with each other to result in a change in shape of the sensing material (e.g., thermally expanded or cracked). Further, in the case where a sensor substrate or a sensor electrode is coated with dispersion solution containing nanoparticles, the nanoparticles may aggregate with each other and thereby have an increased particle size. In this case, the gas sensor may suffer from degraded sensing performance.

By contrast, in the case where a sensing material is formed of coarse (e.g., micrometer-sized) particles, it is possible to realize a gas sensor with extremely high thermal stability. However, since the sensing material composed of the micrometer-sized particles has a specific surface area that is several tens to several hundred times smaller than that of the case that the sensing material composed of the nanoparticles, it is hard to realize an extremely high sensitivity using the sensing material composed of only the microparticles. In particular, for the microparticle-based sensing material, it is impossible to detect minute amounts (e.g., several tens parts per billion (ppb)-one parts per million (ppm)) of volatile organic compound gases, which are contained in an exhalation of a human being. Meanwhile, the sensing material may be composed of a mixture of nanoparticles and microparticles. However, even in this case, the nanoparticles may be stuck on surfaces of the microparticles. Alternatively, the nanoparticles may participate in a nanoparticle-microparticle reaction, which may occur when a high temperature thermal treatment process is performed after coating a surface of a sensor electrode with the nanoparticles and microparticles. As a result, a density or compactness of the sensing material may be increased. Namely, the density or compactness of the sensing material may be too high for the gas sensor to detect a gas concentration of 1 ppm or lower.

Recently, one-dimensional nanowires or nanofibers are being studied for the gas sensor. Due to a large surface to volume ratio and a well-developed pore structure thereof, the use of nanowires or nanofibers allows for the gas sensor to have high sensitivity. However, in this case, since point-like contact regions between the nanowires or nanofibers are only included in a current path, a base resistance of the gas sensor in the air is very high. Accordingly, low resistivity materials (e.g., ZnO or $SnO_2$) are usually used for the nanowires or nanofibers. If a high resistivity material is used, it is necessary to use an instrument capable of precisely measuring such high resistivity.

SUMMARY

Example embodiments provide a composite material including a same kind of metal oxide material, but has differences in shape and mean size, and gas sensors using the composite material as a sensing material thereof. For example, the composite material may include polycrystalline metal oxide semiconductor nanofibers, whose mean diameter ranges from 150 nm to 1 μm, metal oxide semiconductor microparticles, whose mean diameter ranges from 200 nm to 3 μm, and metal oxide semiconductor nanoparticles, whose mean diameter ranges from 10 nm to 100 nm. Accordingly, by using the three different morphologies of metal oxide material, the composite can have an open pore structure, allowing the gas sensor to have high sensitivity, fast response and recovery speeds, and long lifetime stability. In particular, by adjusting relative contents of the three different morphologies of metal oxide material in the composite, it is possible to easily control a base resistance of the gas sensor. Further, other example embodiments provide methods of manufacturing the composite material and the gas sensors.

According to example embodiments, polycrystalline metal oxide nanofibers with a high aspect ratio may be synthesized and be mixed with metal oxide microparticles and metal oxide nanoparticles to form a composite sensing material with a variety of shapes and pore sizes. The composite sensing material may be provided to cover a sensor electrode of a gas sensor. Here, the use of the composite sensing material allows a gas sensor to have high mechanical, thermal, and electrical stabilities. Especially, a gas sensor using only nanofibers as a sensing material thereof (hereinafter, "nanofiber-based gas sensor") suffers from high base resistance, but in the case where the composite sensing material is used, a base resistance of the sensor can be stably controlled. This is because the nanoparticles and the microparticles are provided in large-sized pores between the nanofibers and the nanofibers are in effective contact with each other. Further, the base resistance of the composite sensing material can be controlled by adjusting a composition ratio between the polycrystalline nanofibers, the microparticles, and the nanoparticles.

According to example embodiments, provided are a composite metal oxide sensing material containing polycrystalline nanofibers, microparticles, and nanoparticles, a gas sensor with the same, and a method of manufacturing the same. Here, the polycrystalline nanofibers may be synthesized using an electrospinning method and may have a mean diameter of 150 nm-1 µm.

In example embodiments, the metal oxide semiconductor nanofibers may have a length of 2 µm or longer. For example, the length of the metal oxide semiconductor nanofibers may be at least 5 µm.

In example embodiments, the metal oxide semiconductor microparticles may have a mean diameter of 200 nm-3 µm.

In example embodiments, the metal oxide semiconductor nanoparticles may have a mean diameter of 10 nm-100 nm.

In example embodiments, the gas sensor may include the composite metal oxide sensing material containing the polycrystalline nanofibers, the microparticles, and the nanoparticles, which have weight percentages X, Y, and Z, respectively. Here, X=20-95 wt %, Y=0-80 wt %, Z=0-30 wt %, and X+Y+Z=100 wt %.

According to other example embodiments, a method of manufacturing a gas sensor may include a step (a) of sequentially performing an electrospinning process and a thermal treatment process to synthesize polycrystalline nanofibers made of metal oxide. The electrospinning process may be performed using a polymer-containing solution, in which a precursor salt may be contained. The thermal treatment process may be performed to remove the polymer matrix fibers and thereby form the metal oxide nanofibers from the thermal oxidation of precursor salt dissolved within the polymer fibers. The method may further include a step (b) of synthesizing metal oxide microparticles, a step (c) of synthesizing metal oxide nanoparticles, a step (d) of mixing the polycrystalline nanofibers, the microparticles, and the nanoparticles to synthesize a composite-containing solution having a composition ratio of X:Y:Z, where X=20-95 wt %, Y=0-80 wt %, Z=0-30 wt %, and X+Y+Z=100 wt %, a step (e) of coating a sensor electrode with the composite-containing solution, and a step (f) of thermally treating the sensor electrode to form a composite sensor, and a step (g) of manufacturing at least two composite sensors of different types to manufacture a sensor array.

Further, the method may further include a step (h) of adding nanoparticle catalyst into the composite-containing solution, before the step (e). The step (h) may allow the gas sensor to have further improved sensitivity and gas reaction selectivity. Here, the nanoparticle catalyst includes at least one selected from the group consisting of platinum (Pt), palladium (Pd), silver (Ag), gold (Au), iridium oxide ($IrO_2$), ruthenium oxide ($RuO_2$), and rhodium oxide ($Rh_2O_3$).

In addition, the method may further include a step (i) of adding a graphene-containing solution into the composite-containing solution, before the step (e). The step (i) may allow the gas sensor to have a reduced base resistance and improved response and recovery times.

In certain embodiments, the method may further include a step (j) of adding the nanoparticle catalyst-containing solution and the graphene-containing solution into the composite-containing solution, before the step (e).

In example embodiments, in the step (a), the polymer-containing solution may contain one or more polymeric materials, which can be applied for an electrospinning process. Here, the precursor salt may include at least one metal salt which can form metal oxides such as tin dioxide ($SnO_2$), zinc oxide (ZnO), titanium oxide ($TiO_2$), $In_2O_3$, $Zn_2SnO_4$, tungsten trioxide ($WO_3$), cobalt oxide ($Co_3O_4$), nickel oxide (NiO), vanadium oxide ($V_2O_5$), or copper oxide (CuO). In detail, the electrospinning process may be performed using an electrospinning solution containing, for example, at least one of acetate, chloride, acetylacetonate, nitrate, methoxide, ethoxide, butoxide, isopropoxide, sulfide, oxytriisopropoxide, ethylhexanoate, cetyl ethylhexanoate, butanoate, ethy amide, amide, in which metallic salts are provided. In certain embodiments, a catalyst (e.g., of Pt, Pd, Ag, Au, $IrO_2$, $RuO_2$, and $Rh_2O_3$) may be included in or on the nanofibers, which is made of the metal oxides (e.g., $SnO_2$, ZnO, $TiO_2$, $In_2O_3$, $Zn_2SnO_4$, $WO_3$, $Co_3O_4$, NiO, $V_2O_5$, and CuO). Here, the metal oxide nanofibers or the catalyst-containing metal oxide nanofibers may have a mean diameter ranging from 150 nm to 1 µm.

In the step (b), a conventional solid state reaction may be used to synthesize the metal oxide microparticles having a mean particle diameter of 200 nm-3 µm. However, if the metal oxide microparticles can be synthesized to have such a diameter, there may be no limitation for a synthesis method thereof. After the synthesis of the metal oxide microparticles through solid state reaction, a ball-milling process may be further performed on the metal oxide particles to control sizes of the metal oxide particles.

In the step (c), the metal oxide nanoparticles may be synthesized using a hydrothermal synthesis method or may be manufactured by performing an ultra-fine grinding or microbead ball-milling process on the metal oxide nanofibers manufactured in the step (a). The metal oxide nanoparticles may have a mean diameter of 10 nm-100 nm. The polycrystalline metal oxide nanofibers may comprise of fine nanoparticles having a size of several to several tens of nanometers, and thus, the polycrystalline nanofibers may be ground by the microbead ball-milling process, in which a fine zirconia ball having a size of 0.01-0.1 mm is used. The metal oxide nanoparticles may be contained in a nanoparticle-containing solution. If the metal oxide nanoparticles can be synthesized to have the nano-sized diameter, there may be no limitation for a synthesis method thereof.

In the step (d), the metal oxide semiconductor polycrystalline nanofibers, the metal oxide microparticles, and the metal oxide nanoparticles prepared in the steps (a), (b), and (c) may be added in a solvent material (e.g., water, ethanol, acetone, and DMF), and a small amount of polymer binder or dispersing agent may be added therein and be mixed using a three-dimensional mixer or a ball-milling method. As a result, the composite-containing solution, in which the polycrystalline nanofibers, the microparticles, and the nanoparticles are contained, may be obtained. In the mixing step, the metal oxide polycrystalline nanofibers or the catalyst-containing metal oxide polycrystalline nanofibers manufactured in the step (a) may be cut or chopped into short fibers. Accordingly, the polycrystalline nanofibers may have an aspect ratio of 2-5000.

In the step (e), the composite-containing solution manufactured in the step (d) may be provided to cover a previously-prepared sensor electrode and an insulating substrate using a coating process (e.g., one of screen-printing, drop-coating, spin-coating, inkjet printing, electrohydrodynamic deposition (EHD), and dispensing methods). Here, parallel electrodes for measuring a change in electrical resistance of the composite sensing layers may be formed on the insulating substrate. If the composite of metal oxide nanofibers, microparticles, and nanoparticles can be uniformly coated on the sensor electrode, there may be no limitation for a coating method thereof.

The step (f) may be performed at a high temperature in such a way that the sensing material is well attached to the substrate and the nanofibers, the microparticles, and the nanoparticles are in good contact with each other. Further, the step (f) may be performed in such a way that the resistance change can be measured with improved stability. As an example, the step (f) may be performed at a temperature of 400-800° C. During the step (f), the polymer binder may be decomposed or burned out, and thus, the composite containing the polycrystalline nanofibers, the microparticles, and the nanoparticles may be formed of a carbon-free metal oxide semiconductor material.

In the step (g), the at least two composite sensors may be configured to be different from each other in terms of their composition ratios. At least one of the at least two composite sensors may be manufactured by the steps (a)-(f). In certain embodiments, the at least two composite sensors may include a gas sensor manufactured using a different method from the steps (a)-(f).

As a result of the step (h), nanoparticle catalyst (e.g., including at least one of Pt, Pd, Ag, Au, $IrO_2$, $RuO_2$, or $Rh_2O_3$) may be further contained in or on the nanofibers, the microparticles, or the nanoparticles of the composite sensing material. The catalyst particle may have a size of 1 nm-10 nm. In certain embodiments, the catalyst particle may have a size of 5 nm or less. Nanoparticles of Pt, Pd, Ag, Au, Ir, Ru, or Rh may be synthesized using a polyol process. The catalyst particle-containing solution may be mixed with the composite-containing solution prepared in the step (d) and may be used to manufacture a composite sensing material containing the polycrystalline nanofibers, the microparticles, the nanoparticles, and the catalyst to be used in the step (e). In such a composite sensing material, the catalyst particles may have the smallest size. Thus, the catalyst particles may be uniformly attached to surfaces of the polycrystalline nanofibers, the microparticles, and/or the nanoparticles, and the presence of the catalyst particles may contribute to improve sensitivity and selectivity of the sensor.

As a result of the step (i), graphene as a catalyst material as well as charge transport supporting layer may be further contained in or on the nanofibers, the microparticles, or the nanoparticles of the composite sensing material. Accordingly, the composite sensing material may be configured to contain the polycrystalline nanofibers, the microparticles, the nanoparticles, and the graphene. The graphene may include at least one of non-oxidized graphene, oxidized graphene, reduced graphene oxide, or very thin graphite. The graphene may have a weight percent of 0.01-2 wt % in the composite sensing material. Due to its good electrical conduction property, the graphene may contribute to control the base resistance and the response time of the gas sensor.

As a result of the step (j), the composite sensing material may be manufactured to further contain the catalyst of the step (h) and the graphene of the step (i). That is, in the step (j), the nanoparticle catalyst-containing solution and the graphene-containing solution may be mixed with the composite-containing solution. Accordingly, the composite sensing material may contain the polycrystalline nanofibers, the microparticles, the nanoparticles, the catalyst, and the graphene.

The gas sensor manufactured by the afore-described method may include a sensing material, in which the polycrystalline nanofibers, the microparticles, and the nanoparticles are contained in a composition ratio of X:Y:Z, where X=20-95 wt %, Y=0-80 wt %, Z=0-30 wt %, and X+Y+Z=100 wt %. The gas sensor may be used as a part of a sensor array. The gas sensor or the sensor array may be used to detect a harmful gas or a specific gas contained in an exhalation of a human being. For example, the gas sensor or the sensor array may be used to diagnose a disease.

BRIEF DESCRIPTION OF THE DRAWINGS

Example embodiments will be more clearly understood from the following brief description taken in conjunction with the accompanying drawings. The accompanying drawings represent non-limiting, example embodiments as described herein.

Figure 1:
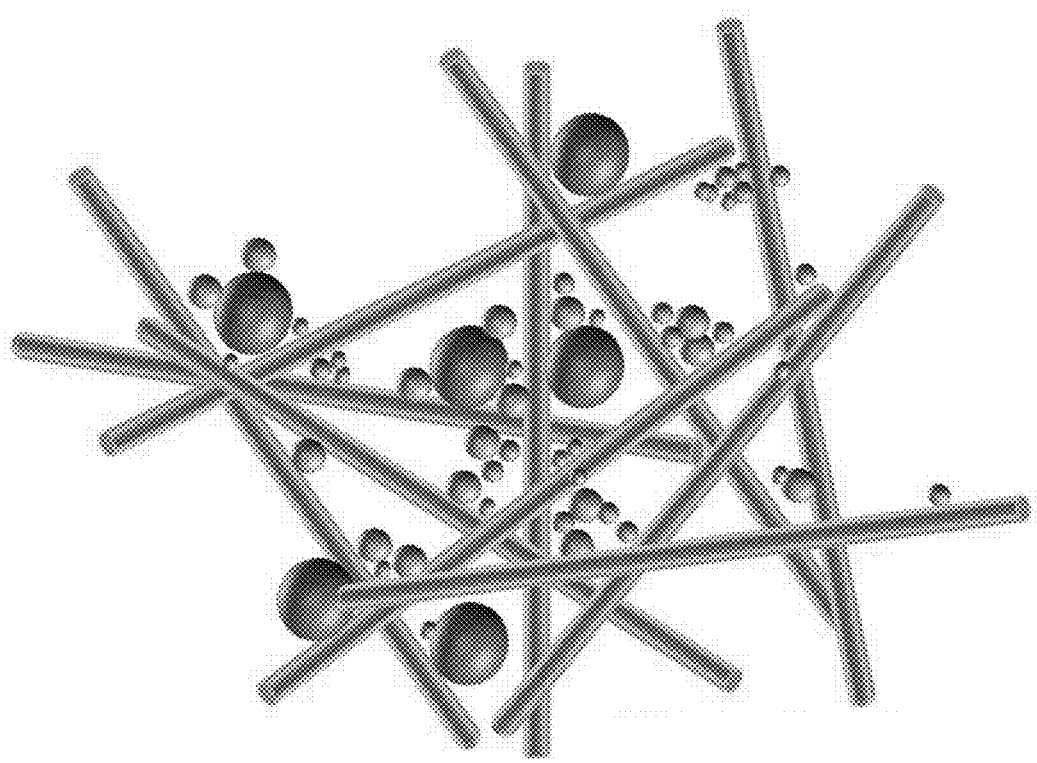
FIG. 1 is a schematic diagram illustrating a sensing material including polycrystalline nanofibers, microparticles, and nanoparticles, which are made of a metal oxide semiconductor material, according to example embodiments.
Figure 1:
Figure 1:
Figure 1:

It should be noted that these figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION

Example embodiments of the inventive concepts will now be described more fully with reference to the accompanying drawings, in which example embodiments are shown. Example embodiments of the inventive concepts may, however, be embodied in many different forms and should not be construed as being limited to the embodiments set forth herein; rather, these embodiments are provided so that this disclosure will be thorough and complete, and will fully convey the concept of example embodiments to those of ordinary skill in the art. In the drawings, the thicknesses of layers and regions are exaggerated for clarity. Like reference numerals in the drawings denote like elements, and thus their description will be omitted.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Like numbers indicate like elements throughout. As used herein the term "and/or" includes any and all combinations of one or more of the associated listed items. Other words used to describe the relationship between elements or layers should be interpreted in a like fashion (e.g., "between" versus "directly between," "adjacent" versus "directly adjacent," "on" versus "directly on").

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises", "comprising", "includes" and/or "including," if used herein, specify the presence of stated features, integers, steps, operations, elements and/or components, but do not preclude the presence or addition of one or more other features, integers, steps, operations, elements, components and/or groups thereof.

Unless otherwise defined, all terms (including technical and scientific terms) used herein have the same meaning as commonly understood by one of ordinary skill in the art to which example embodiments of the inventive concepts belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

According to example embodiments, a composite material including at least one of polycrystalline nanofibers, microparticles, and nanoparticles may be used as a sensing material of, for example, a gas sensor. The use of such a composite material allows the gas sensor to overcome the afore-described technical difficulties in the conventional gas sensors having only the one type of sensing material (e.g., polycrystalline nanofibers, microparticles, or nanoparticles). For example, by using the gas sensor described below, it is possible to overcome all of low stability in a nanoparticle-based sensor, low sensitivity in a microparticle-based sensor, and high base resistance in a nanofiber-based sensor. In other words, according to example embodiments herein, the gas sensor can be configured or manufactured to have high sensitivity, high response speed, and high reliability.

FIG. 1 is a schematic diagram exemplarily illustrating a structure of a composite-based sensing material 500, which includes metal oxide nanoparticles 100, metal oxide microparticles 200, and metal oxide polycrystalline nanofibers 300, according to example embodiments.

Referring to FIG. 1, each of the metal oxide polycrystalline nanofibers 300 may have a high aspect ratio. The metal oxide polycrystalline nanofibers 300 may be formed as a network structure, and thus, large-sized pores may be formed between the metal oxide polycrystalline nanofibers 300. The large-sized pores between the metal oxide polycrystalline nanofibers 300 may have a mean size ranging from several micrometers to several tens of micrometers. Accordingly, the metal oxide polycrystalline nanofibers 300 may allow a gas to diffuse and permeate easily through the large-sized pores. However, the metal oxide polycrystalline nanofibers 300 may be in point contact with each other at intersections therebetween and consequently lead to an increase in base resistance of a gas sensor.

The metal oxide microparticles 200 may be distributed in the large-sized pores or between the metal oxide polycrystalline nanofibers 300 and may be attached to the metal oxide polycrystalline nanofibers 300 to increase a density or compactness of the sensing material. For example, the compactness or density of the sensing material may be higher when it further includes the metal oxide microparticles 200 than when it includes only the metal oxide polycrystalline nanofibers 300.

The metal oxide nanoparticles 100 may be attached to the metal oxide polycrystalline nanofibers 300 and/or the metal oxide microparticles 200. The presence of the metal oxide nanoparticles 100 may contribute to further increase a surface area of the metal oxide polycrystalline nanofibers 300 or the metal oxide microparticles 200. In certain embodiments, the metal oxide nanoparticles 100 may be aggregated to form metal oxide nanoparticle aggregates 400. The metal oxide nanoparticle aggregates 400 may be disposed to partially fill gaps or pores between the metal oxide microparticles 200 and/or the metal oxide polycrystalline nanofibers 300.

Since the metal oxide polycrystalline nanofibers 300, the metal oxide nanoparticles 100, and the metal oxide microparticles 200 are included in the composite sensing material 500 in an intermixed manner, the composite sensing material 500 can have high compactness and be abundant in minute pores. Accordingly, a sensor using the composite sensing material 500 as the sensing material thereof can detect stably a change in electrical resistance. Especially, the use of the composite sensing material 500 may allow the sensor to have excellent thermal stability, even when a detection test should be repeatedly performed at a high temperature condition (for example, of about 300° C. or higher) required for a normal operation of the sensor.

Even in the case that the pores between the metal oxide polycrystalline nanofibers 300 are filled with the metal oxide microparticles 200 and the metal oxide nanoparticles 100, pores may be formed at least between the metal oxide nanoparticles 100, between the metal oxide microparticles 200, between the metal oxide polycrystalline nanofibers 300 and the metal oxide microparticles 200, and/or between the metal oxide polycrystalline nanofibers 300 and the metal oxide nanoparticles 100. In other words, various pores, whose mean size ranges from 0.1 nanometers to several tens of micrometers, may exist in the composite sensing material 500.

In the composite sensing material 500, the polycrystalline nanofibers 300, the microparticles 200, and the nanoparticles 100 may be contained in a composition ratio of X:Y:Z, respectively, where X ranges from 20 to 95 wt %, Y ranges from 0 to 80 wt %, Z ranges from 0 to 30 wt %, and X+Y+Z=100 wt %. In the sensor or a sensor array therewith, the composition ratio between the polycrystalline nanofibers, the microparticles, and the nanoparticles may be changed or adjusted to improve sensing selectivity of the composite sensing material 500, under the above condition.

Figure 2:
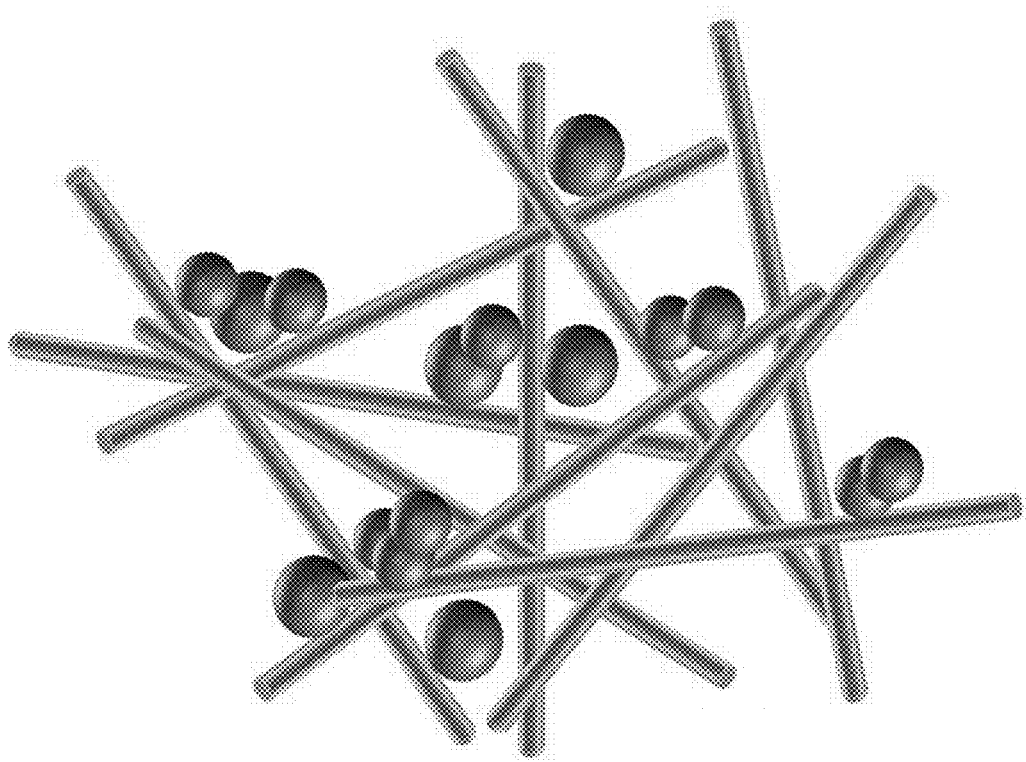
FIG. 2 is a schematic diagram illustrating a sensing material including polycrystalline nanofibers and microparticles, which are made of a metal oxide semiconductor material, according to other example embodiments.
Figure 2:
Figure 2:

Meanwhile, the metal oxide nanoparticles 100 are easily aggregated to form the metal oxide nanoparticle aggregates 400 as shown in FIG. 1 and the metal oxide nanoparticles 100 are expensive at present. In this respect, the sensing material may be manufactured without the metal oxide nanoparticles 100. For example, as shown in FIG. 2, a composite sensing material 600 may be manufactured to include the metal oxide polycrystalline nanofibers 300 and the metal oxide microparticles 200. Referring to FIG. 2, in the composite sensing material 600, the metal oxide microparticles 200 may be disposed between the metal oxide polycrystalline nanofibers 300. The metal oxide microparticles 200 may be robustly attached to the metal oxide polycrystalline nanofibers 300, and this may contribute to increase transport of electrons or holes flowing through the composite sensing material 600 and thereby reduce response and recovery times in an event of gas detection. Further, the use of the composite sensing material 600 may allow for improvement in structural and long lifetime stabilities of the gas sensor, compared with the case that only the metal oxide polycrystalline nanofibers 300 are used for the sensing material.

In the composite sensing material 600, the polycrystalline nanofibers and the microparticles may be contained in a composition ratio of X:Y, respectively, where X ranges from 10 to 90 wt %, Y ranges from 10 to 90 wt %, and X+Y=100 wt %. Here, an increase in content of the metal oxide microparticles 200 may allow for the improvement in structural and long lifetime reliabilities of the composite sensing material 600 but lead to a reduction in specific surface area of the composite sensing material 600 and consequently deterioration in sensitivity of the sensor. In this respect, the metal oxide polycrystalline nanofibers 300 may be provided to have a weight percentage of 10% or higher than the metal oxide microparticles 200. By using the composite sensing material 600 including the metal oxide polycrystalline nanofibers 300 and the metal oxide microparticles 200, it is possible to overcome the issue of high base resistance, which may occur in a sensing material having only the metal oxide polycrystalline nanofibers 300. In particular, in the case where the sensing material is composed of only the metal oxide polycrystalline nanofibers 300 made of a low conductivity material (e.g., $Zn_2SnO_4$), a base resistance (i.e., electric resistance of the sensing material measured in the air) of the sensing material may be excessively high. For example, since such a gas sensor may be operated at a high temperature of 450° C. or higher, there may be technical issues such as excessively high power consumption, unstable gas adsorption/desorption characteristics, and unstable operational characteristics. In this respect, in the case where the composite sensing material 600 is composed of only the polycrystalline nanofibers and the microparticles, the microparticles may be contained in the composite sensing material 600 to have a weight percent that is higher than 10 wt % but lower than 90 wt %. This may allow the gas sensor to have improved detection performance.

In certain embodiments, unlike those of FIGS. 1 and 2, the composite sensing material may consist of the metal oxide polycrystalline nanofibers 300 and the metal oxide nanoparticles 100. For example, in such a composite sensing material, the polycrystalline nanofibers and the nanoparticles may be contained in a composition ratio of X:Z, respectively, where X ranges from 10 to 90 wt %, Z ranges from 10 to 90 wt %, and X+Z=100 wt %.

Figure 3:
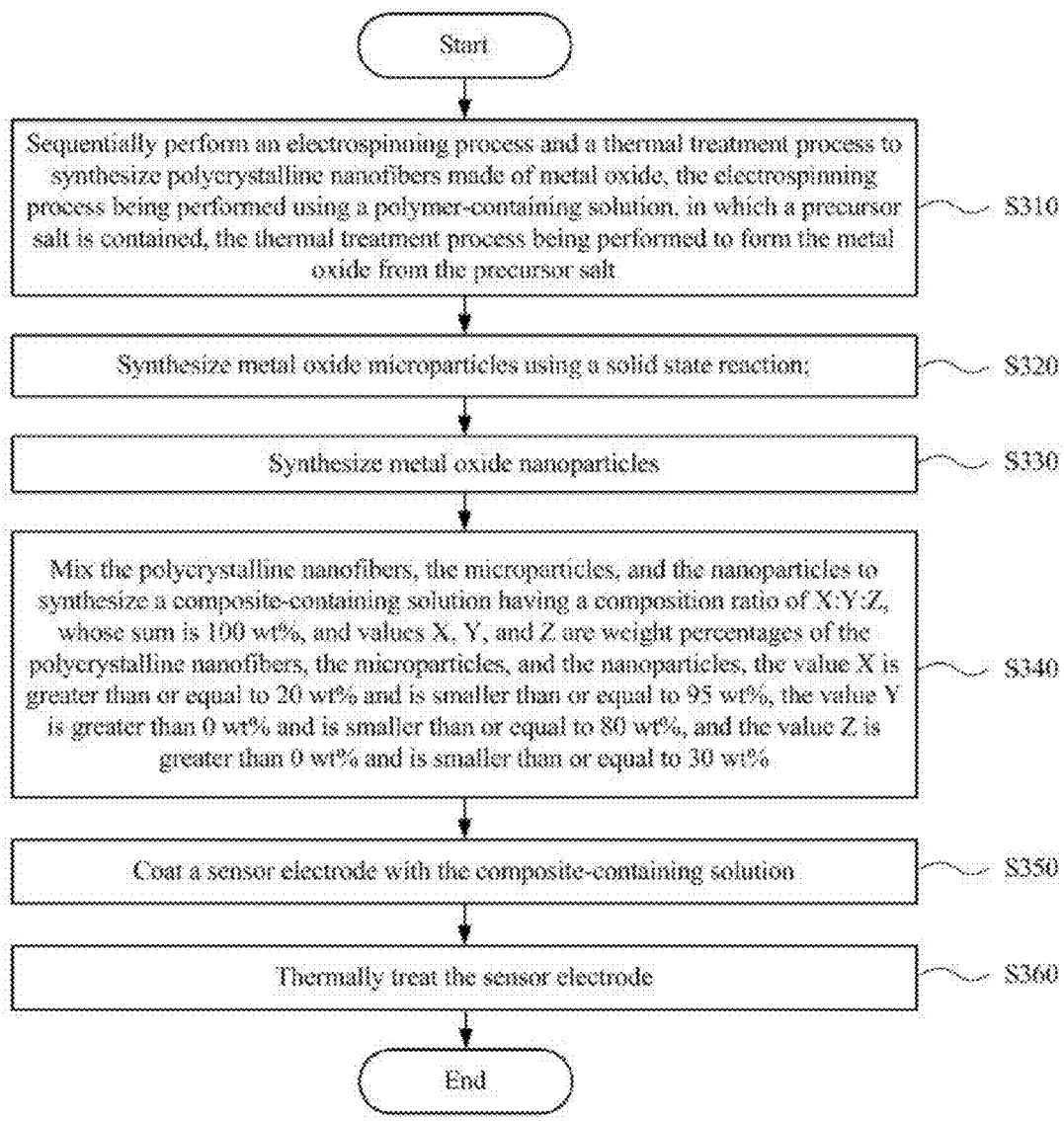
FIG. 3 is a flowchart illustrating a method of manufacturing a composite sensor according to example embodiments

FIG. 3 is a flowchart illustrating a method of manufacturing a composite sensor according to example embodiments The method of manufacturing a gas sensor may include a step S310 of sequentially performing an electrospinning process and a thermal treatment process to synthesize polycrystalline nanofibers made of metal oxide, the electrospinning process being performed using a polymer-containing solution, in which a precursor salt is contained, the thermal treatment process being performed to form the metal oxide from the precursor salt, a step S320 of synthesizing metal oxide microparticles using a solid state reaction, a step S330 of synthesizing metal oxide nanoparticles, a step S340 of mixing the polycrystalline nanofibers, the microparticles, and the nanoparticles to synthesize a composite-containing solution having a composition ratio of X:Y:Z, whose sum is 100 wt %, and values X, Y, and Z are weight percentages of the polycrystalline nanofibers, the microparticles, and the nanoparticles, the value X is greater than or equal to 20 wt % and is smaller than or equal to 95 wt %, the value Y is greater than 0 wt % and is smaller than or equal to 80 wt %, and the value Z is greater than 0 wt % and is smaller than or equal to 30 wt %, a step S350 of coating a sensor electrode with the composite-containing solution, and a step S360 of thermally treating the sensor electrode.

Hereinafter, the inventive concept will be described in more detail with respect to example embodiments but will not be limited to the following example embodiments.

First Embodiment

Synthesis of Tin Oxide Nanofibers

An electrospinning solution was prepared by mixing 0.200 g poly(vinyl pyrrolidone) (PVP, molecular weight 1,300,000 g/mol, Aldrich) and 0.200 g poly(methyl methacrylate) (PMMA, molecular weight 350,000 g/mol, Aldrich), adding the mixture in 2.831 g N,N-dimethylformamide (DMF) solution, in which 0.400 g tin acetate(IV) (Aldrich) serving as a tin oxide precursor and 0.110 g acetic acid (Junsei Chemical) were contained, and agitating the resulting mixture at 500 RPM for about 48 hours at 25° C. The electrospinning solution containing the tin oxide precursor and the PVP-PMMA polymer was supplied in a syringe and was spun at a flow rate of 10 μm per minute using a syringe pump (Henke-Sass Wolf, 10 ml NORM-JECT). A voltage of 15 kV was applied between a needle (25 gauge) for spinning the electrospinning solution and a current collector substrate for collecting a nanofiber web to manufacture a nanofiber web of tin oxide precursor/PVP-PMMA composite polymer.

Figure 4:
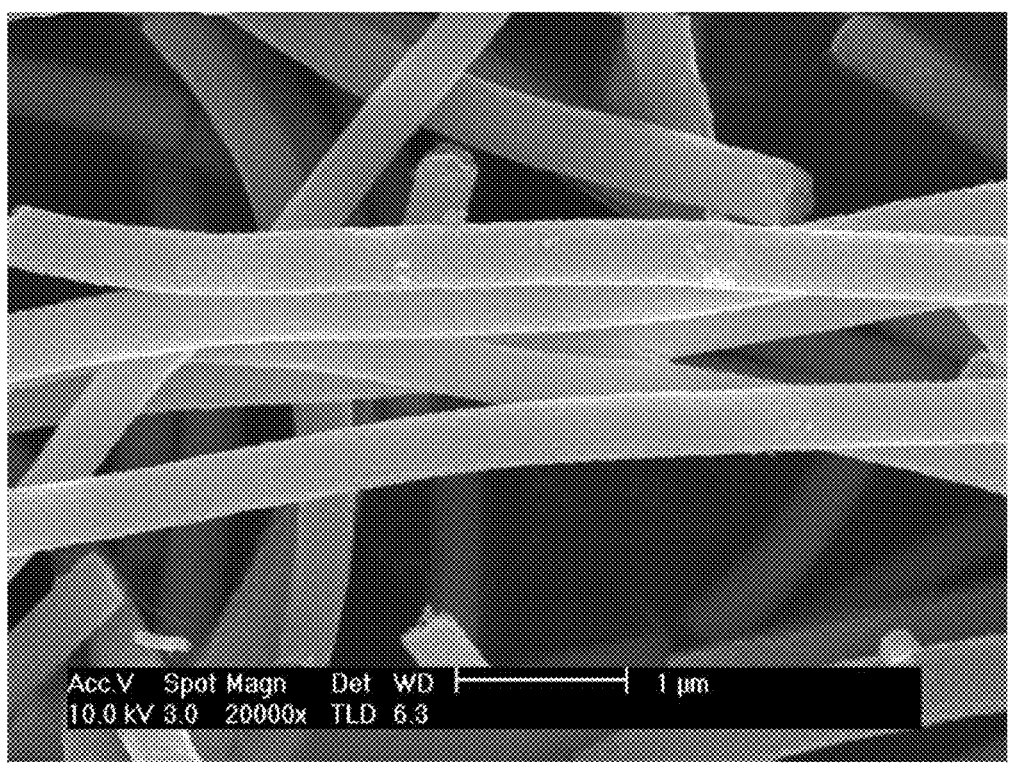
FIG. 4 is a scanning electron microscope (SEM) image of tin oxide nanofibers, which were manufactured by an electrospinning method, according to a first embodiment.

The manufactured nanofiber web of tin oxide precursor/PVP-PMMA composite polymer was thermally treated in an air ambient for 30 minutes at a high temperature of 500° C. using a small electric furnace (Vulcan 3-550, Ney). Here, the temperature was increased and decreased at a constant rate of 4° C./min. As a result of the high-temperature thermal treatment, the PVP-PMMA polymers in the tin oxide precursor/PVP-PMMA composite polymer nanofiber web were decomposed or burned out, and tin oxide precursors existing in the polymer fibers were oxidized to form tin oxide nanofibers. FIG. 4 shows a scanning electron microscope (SEM) image of the tin oxide nanofibers, which were manufactured by an electrospinning method according to the first embodiment of the inventive concept. From the surface morphology inspection on the tin oxide nanofibers, the tin oxide nanofibers were found to have a mean diameter of about 360 nm. Further, each of the nanofibers consisted of polycrystalline nanoparticles and had a nanofiber-shaped structure. This result shows that the above electrospinning method can be used to easily manufacture tin oxide nanofibers with a uniform diameter.

Second Embodiment

Synthesis of Tin Oxide Nanofiber-Nanoparticle Composite

Figure 5:
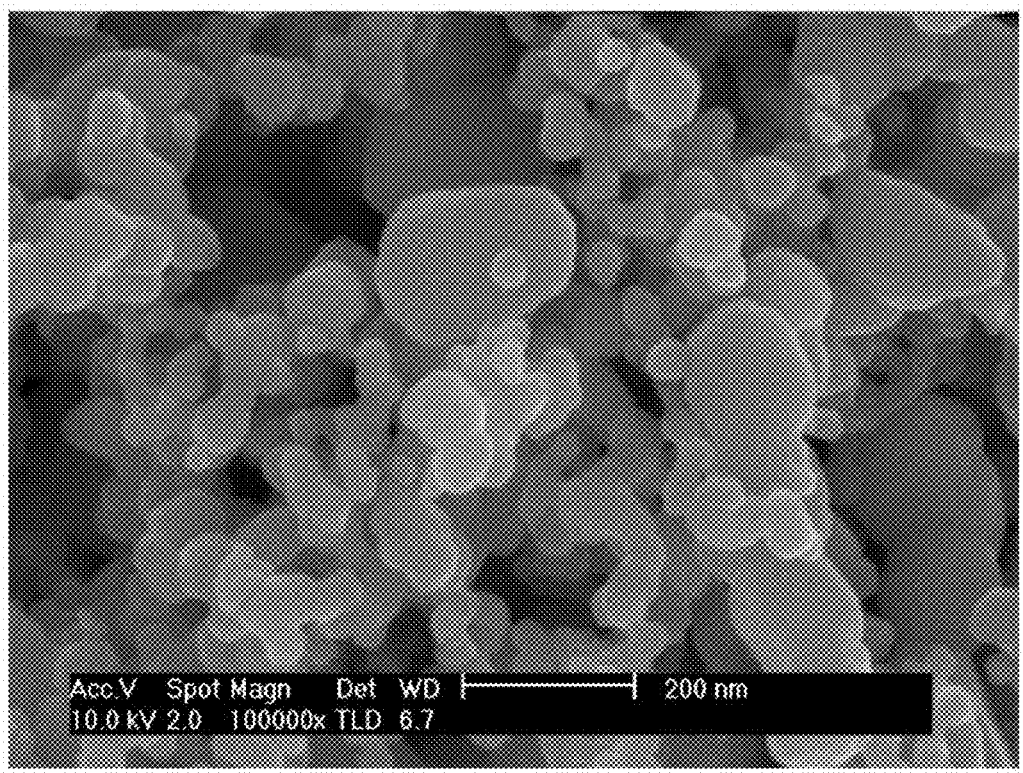
FIG. 5 is a SEM image of tin oxide nanoparticles, according to a second embodiment.

A composite sensing material containing the tin oxide nanofibers and the tin oxide nanoparticles (hereinafter, "tin oxide nanofiber-nanoparticle composite") was synthesized using tin oxide nanoparticles having a mean size of 100 nm or less. The tin oxide nanoparticles were purchased from Aldrich Co. FIG. 5 shows a SEM image of the tin oxide nanoparticles purchased from Aldrich Co. A plurality of particles had sizes ranging from 40 nm to 60 nm, and some particles had sizes of about 200 nm. Although purchased nanoparticles were used for the present embodiment, if particles are synthesized to have a size of 10 nm-100 nm, there may be no limitation for a synthesis method thereof.

To form the composite material containing tin oxide nanofibers and tin oxide nanoparticles, the tin oxide nanofibers, which were manufactured using the electrospinning method according to the first embodiments, and the tin oxide nanoparticles purchased from Aldrich Co., were mixed with ethanol in a single vial to form a composite. To uniformly mix the composite in the vial, an ultrasonic cleaner was used for about 30 minutes. The tin oxide nanofibers and the tin oxide nanoparticles were contained in the composite sensing material to have a mixing ratio in weight of 8:2.

Figure 6:
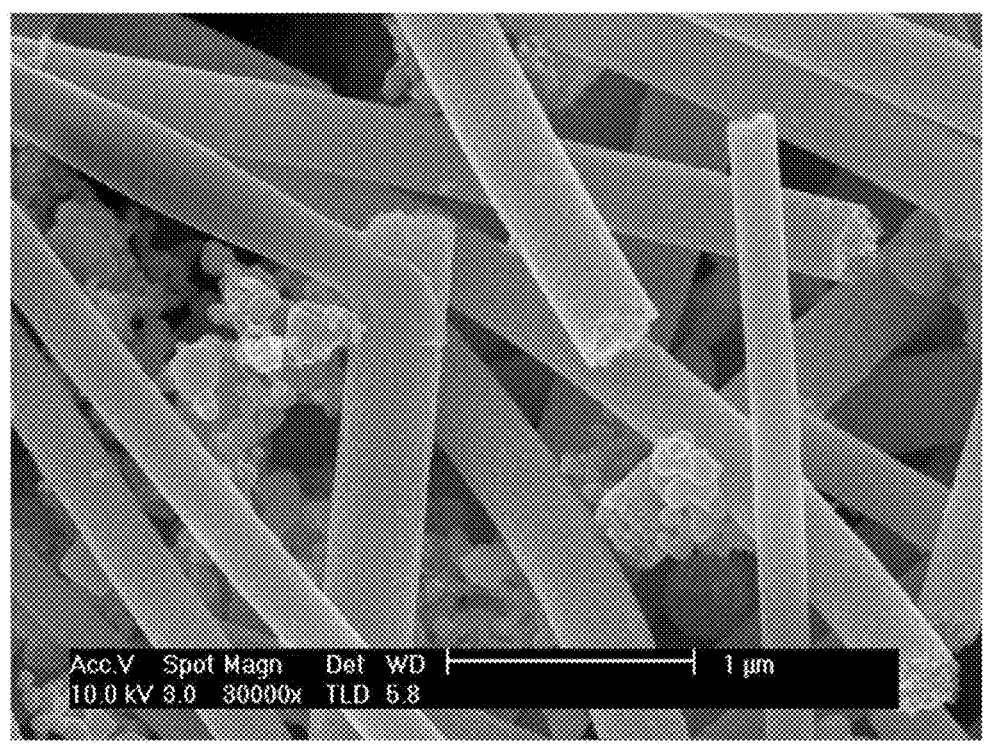
FIG. 6 is a SEM image of a composite including tin oxide nanofibers and tin oxide nanoparticles, according to the second embodiment.

FIG. 6 is a SEM image of the tin oxide nanofiber-nanoparticle composite, according to the second embodiment. FIG. 6 shows that, in the composite material, the tin oxide nanoparticles were distributed between the tin oxide nanofibers and were relatively well attached to the nanofibers. As shown in FIG. 6, there were aggregates of nanoparticles in the composite material. Further, when compared with the structure of FIG. 4, it was found that the composite material of FIG. 6 had more compact and stable structure. The increase in compactness of the composite material leads to an increase in area of a surface for reaction with a gas. However, a composite material with uniformly-distributed nanoparticles may be preferred, when compared with a composite material with excessively-aggregated nanoparticles.

Third Embodiment

Synthesis of Zinc Stannate Nanofibers

Zinc stannate nanofibers were synthesized by preparing polymer nanofibers containing zinc precursors and tin precursors and thermally treating the polymer nanofibers. 0.355 g tin acetate (IV) (Aldrich) was used as the tin precursors, 0.414 g zinc acetate (Aldrich) was used as the zinc precursors. The polymer contained 0.626 g poly(vinyl acetate) (PVAc, molecular weight 500,000 g/mol). The polymer mixed with the tin and zinc precursors was added in 3.747 g N,N-dimethylformamide (DMF) solution and was agitated at 500 RPM for about 24 hours at 25° C. to form an electrospinning solution.

Figure 7:
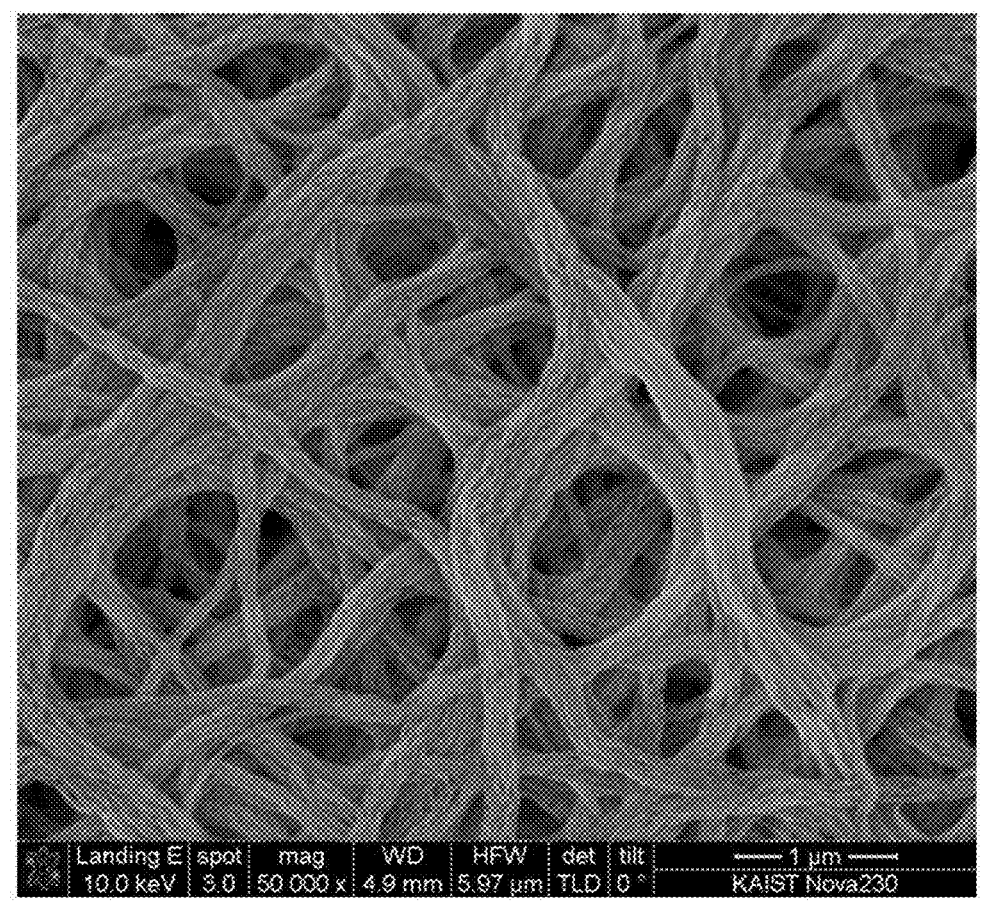
FIG. 7 is a SEM image of zinc stannate ($Zn_2SnO_4$) nanofibers, according to a third embodiment.

The PVAc polymer containing the zinc and tin precursors was thermally treated in an air ambient to form nanofibers of zinc stannate (e.g., $Zn_2SnO_4$). The thermal treatment was performed in a small electric furnace (Vulcan 3-550, Ney). Further, during the thermal treatment, a temperature of the furnace was increased up to 700° C. at a rate of 5° C./min, was maintained for one hour, and was decreased to the room temperature at the rate of 5° C./min. As a result of the high-temperature thermal treatment, polymer in the nanofibers was decomposed or burned out, and the zinc and tin precursors in the polymer were oxidized to form zinc stannate. FIG. 7 is a SEM image of zinc stannate ($Zn_2SnO_4$) nanofibers, which were manufactured by the electrospinning method according to the third embodiment. The zinc stannate nanofibers had a porous and well-developed network structure and each of them had a mean diameter of 150-200 nm. Since the poly (vinyl) acetate (PVAc) has very low miscibility with the zinc and tin precursors, a phase separation may occur in an initial stage of the electrospinning process, and this may lead to formation of many pores in the nanofibers. As solvent is volatilized, the phase separation and solidification may occur quickly. For example, as a result of the phase separation, a precursor-rich region with abundant tin and zinc precursors may be separated from a polymer-rich region to form nanofibers. During the thermal treatment process, the polymer-rich region may be removed to form the pores, and the precursor-rich region may be oxidized to form zinc stannate. Therefore, after the thermal treatment process, the zinc stannate nanofibers may have a well-developed porous structure.

Fourth Embodiment

Synthesis of Zinc Stannate Microparticles

To form zinc stannate microparticles, single-phase zinc stannate ($Zn_2SnO_4$) bulk particles were synthesized using a solid state reaction, and then, a ball-milling process was further performed to control sizes of the microparticles. To synthesize the zinc stannate microparticles, 10.851 g zinc oxide (ZnO) powder (Aldrich 99.9%) and 10.047 g tin oxide ($SnO_2$) powder (Aldrich 99.99%) were mixed in a mole ratio of 2:1 in solvent ethanol to form a solution. A zirconia ball was plunged into the solution, and then, a ball-milling process was performed at about a speed of 200 tacho meter per minute for 24 hours.

Figure 8:
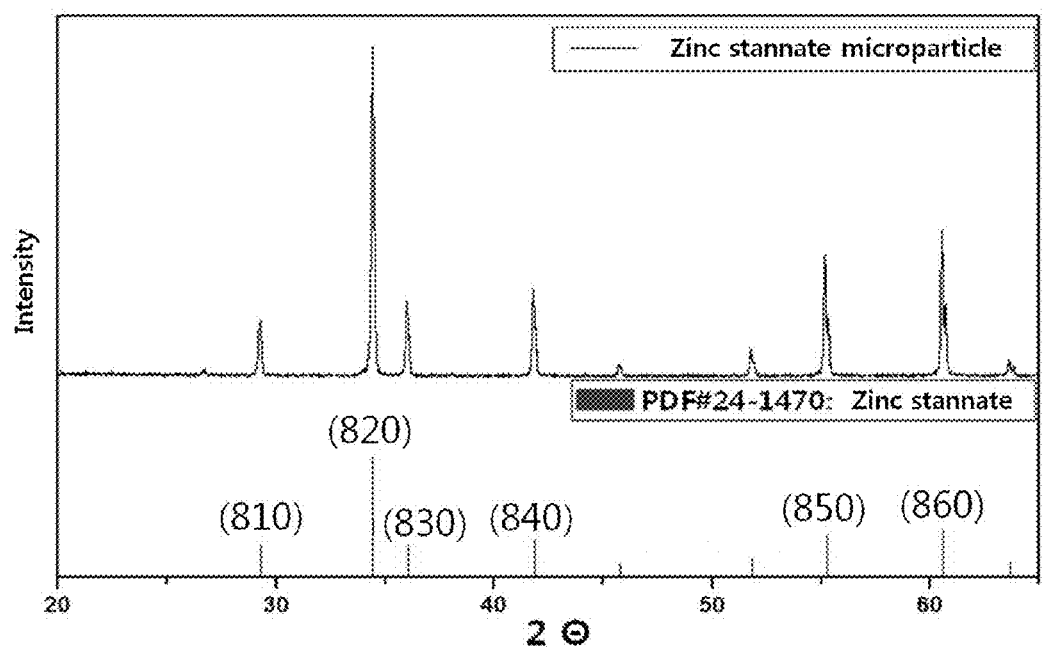
FIG. 8 is a graph illustrating an X-ray diffraction result of zinc stannate microparticles, which were manufactured by a solid-state reaction method, according to a fourth embodiment.

Thereafter, the solution was moved into a beaker, was agitated at 120 RPM at 200° C. to evaporate all the ethanol, and then, was thermally treated at 1200° C. for 3 hours. In the thermal treatment, a process temperature was increased at a rate of 4° C./min in an electric furnace and was quenched in the air. Due to the use of the high temperature thermal treatment, as confirmed by an X-ray diffraction (XRD) experiment of FIG. 8, single-phase zinc stannate ($Zn_2SnO_4$) microparticles were well formed, while zinc oxide or tin oxide was almost not formed. FIG. 8 is an XRD graph of a zinc stannate micropowder, which were manufactured by the solid-state reaction, according to the fourth embodiment. As shown in FIG. 8, (810), (820), (830), (840), (850), and (860) planes of inverse spinel zinc stannate ($Zn_2SnO_4$) were clearly found.

Figure 9:
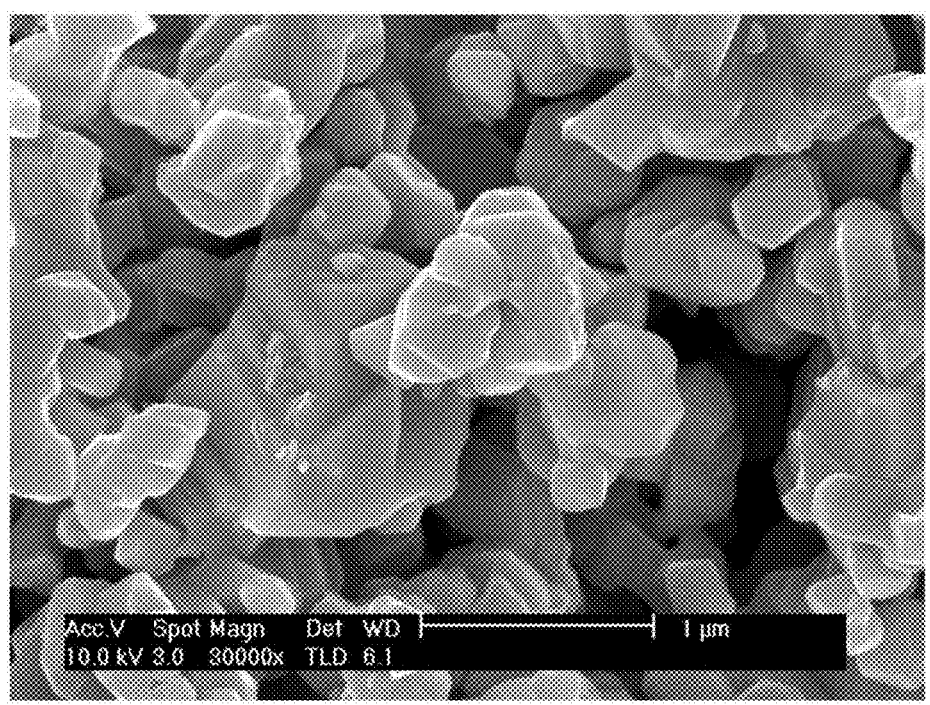
FIG. 9 is a SEM image of zinc stannate microparticles, which were manufactured by the solid-state reaction method, according to the fourth embodiment.

FIG. 9 is a SEM image of zinc stannate microparticles, which were manufactured by the solid-state reaction method, according to the fourth embodiment. Similar to a coating process on a sensor, zinc stannate microparticles was dispersed in ethanol, and the dispersed zinc stannate microparticles were provided to cover a silicon wafer. As shown in FIG. 9, the zinc stannate microparticles had a large mean diameter ranging from 0.5 to 1.8 µm. This is because sizes of some particles were coarsened by the thermal treatment. Further, FIG. 9 shows that if only the microparticles are formed, the particles are excessively aggregated to form a very dense structure.

Fifth Embodiment

Synthesis of Zinc Stannate Nanofiber-Microparticle Composite

Figure 10:
FIG. 10 is a SEM image of a composite including zinc stannate nanofibers and zinc stannate microparticles, according to a fifth embodiment.

To form a zinc stannate nanofiber-microparticle composite, the zinc stannate nanofibers and the zinc stannate microparticles prepared in the third and fourth embodiments were mixed with ethanol in a single vial to form a composite. To uniformly mix the composite in the vial, an ultrasonic cleaner was used for about 30 minutes. The zinc stannate nanofibers and the zinc stannate microparticles were contained in the zinc stannate nanofiber-microparticle composite to have a mixing ratio in weight of 6:4. FIG. 10 is a SEM image of the zinc stannate nanofiber-microparticle composite, according to a fifth embodiment. The microparticles were uniformly distributed between the nanofibers, as intended in the present invention. In certain embodiments, an additional mixing process (for example, using an ultrasonic cleaner or a three-dimensional mixer) or a ball-milling process may be further performed to improve mixing uniformity of the zinc stannate nanofiber-microparticle composite. This may prevent the microparticles from being excessively aggregated in the zinc stannate nanofiber-microparticle composite. As a result of the mixing process, the long zinc stannate nanofibers shown in FIG. 7 were cut or chopped into short zinc stannate nanofibers as shown in FIG. 10. Due to the reduction in length of the nanofibers, the nanofibers can have an increased specific surface area, and this makes it possible to improve attachment and connection properties between the zinc stannate nanofibers and the microparticles, as shown in FIG. 10.

Sixth Embodiment

Evaluation of Performance of Gas Sensor

An experiment to evaluate gas detection performance of several types of gas sensors was performed. Some of the gas sensors were configured to use the tin oxide nanofibers, the tin oxide nanoparticles, and the tin oxide nanofiber-nanoparticle composite manufactured in the first and second embodiments as sensing materials thereof. The others were configured to use the zinc stannate nanofibers, the zinc stannate microparticles, and the zinc stannate nanofiber-microparticle composite manufactured in the third, fourth, and fifth embodiments as sensing materials thereof. In order to evaluate the gas detection performance, sensitivities of the gas sensors were tested using hydrogen sulfide ($H_2S$), acetone ($CH_3COCH_3$), and toluene ($C_7H_8$) gases. In the experiment, Agilent 34972A was used to measure and record a change in electric resistance of each sensor, which was caused by the presence of a specific gas. The gas response was calculated by a formula of $R_a/R_g$, where $R_a$ and $R_g$ denote electric resistances of each sensor in the air and a target gas, respectively. To evaluate the sensitivity of the sensor on a gas concentration, a concentration of the gas was sequentially changed to have five different values of 5 ppm, 4 ppm, 3 ppm, 2 ppm, and 1 ppm, during measuring the electric resistance of each sensor.

Figure 11:
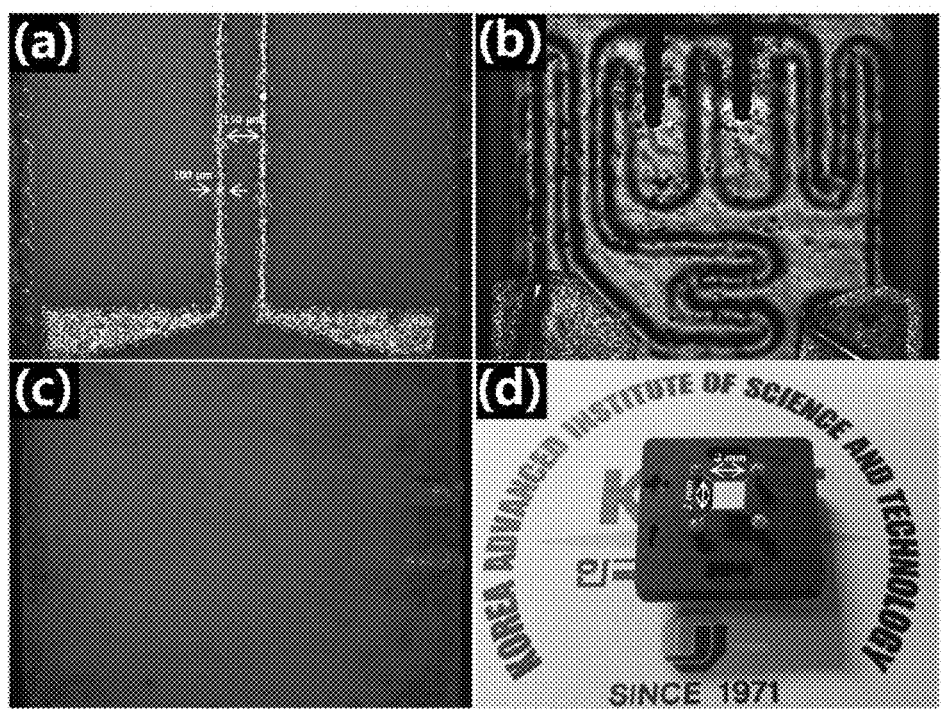
FIG. 11 is a diagram respectively showing optical microscope (OM) images (a)-(c) of an alumina substrate electrode, a heater, and a substrate coated with a sensing material, which are used for a sensor according to example embodiments, and a picture (d) of the sensor therewith.

To manufacture the sensors with the sensing materials of the second and fifth embodiments, a drop coating process was performed to coat an alumina substrate was coated with the tin oxide nanoparticle-nanofiber composite and the zinc stannate nanofiber-microparticle composite provided in ethanol, and then, a wire bonding process was performed to form a single sensor connected to a sensor base. The images (c) and (d) of FIG. 11 show the sensing material coated on the alumina substrate by the drop coating process and the wire-bonded sensor, respectively. An alumina ($Al_2O_3$) substrate of FIG. 11 was used as a substrate for testing the gas sensor, and as shown in the image (b) of FIG. 11, a micro heater was equipped on a 2 mm×2 mm back side of the substrate. A DC voltage was applied to the micro heater using a DC voltage generator (Agilent, E3647A) to change a temperature of the substrate from 200° C. to 450° C., and the sensitivities of the sensor for gases were measured under such a temperature condition. As shown in the image (a) of FIG. 11, Au parallel electrodes spaced 150 µm from each other were formed on a top surface of the alumina substrate to measure a change in resistance therebetween. Here, a width of each Au electrode was 100 μm. In order to provide a test environment similar to that of an exhalation gas discharged from the respiratory system of the human body, the experiment was performed at relative humidity of 85-95%.

Figure 12:
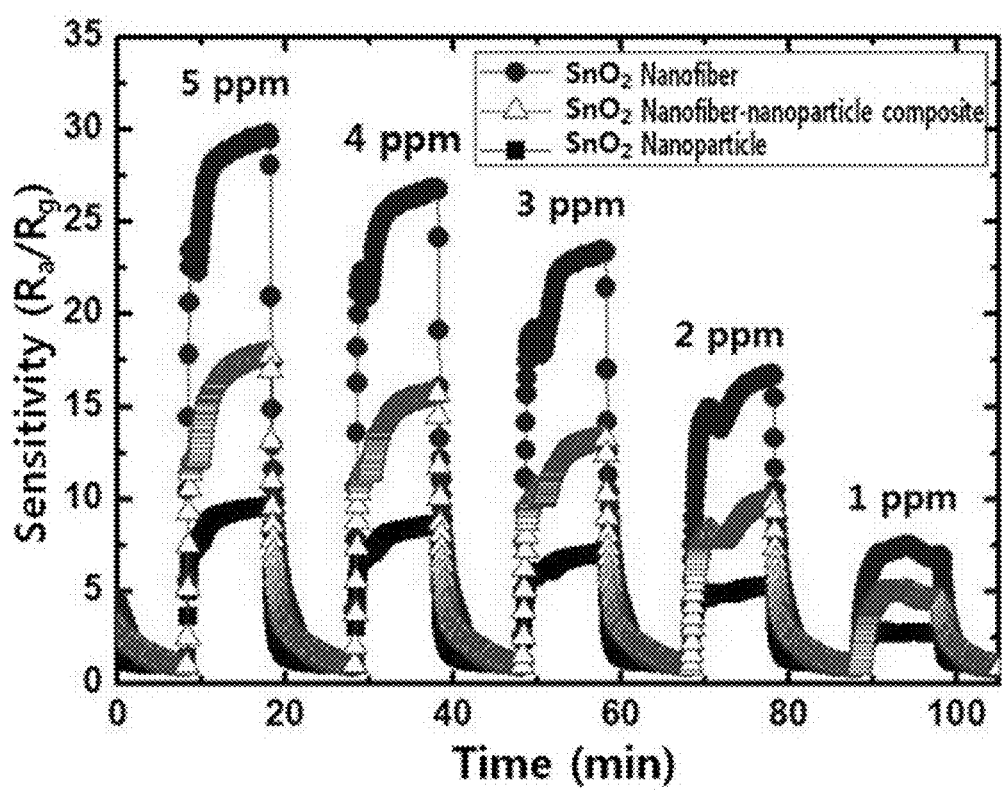
FIG. 12 is a graph showing reactivity characteristics of gas sensors for hydrogen sulfide ($H_2S$) gas at 300° C. Here, sensing materials of the gas sensors were the tin oxide nanofibers, the tin oxide nanoparticles, and the composite including the tin oxide nanofibers and the tin oxide nanoparticles, according to the first and second embodiments o.

FIG. 12 is a graph showing reactivity characteristics of gas sensors for hydrogen sulfide ($H_2S$) gas at 300° C. Here, sensing materials of the gas sensors were the tin oxide nanofibers, the tin oxide nanoparticles, and the tin oxide nanofiber-nanoparticle composite, according to the first and second embodiments of the inventive concept. As shown in FIG. 12, when the sensing material consists of only the tin oxide nanofibers, the gas sensor showed the most superior gas response (i.e., $R_a/R_g$). When the gas sensors were exposed to 5 ppm hydrogen sulfide ($H_2S$) gas, the gas response $R_a/R_g$ was 29.778 for the tin oxide nanofibers and was 9.615 for the tin oxide nanoparticles. That is, the gas response for the tin oxide nanofibers was about three times higher than that for the tin oxide nanoparticles. In the case of the tin oxide nanofiber-nanoparticle composite, the gas response of the gas sensor was 17.859, which was an intermediate value between those of the other two cases. The gas response of the nanofiber-nanoparticle composite sensing material was slightly lower than that of the nanofiber sensing material, but due to the nanoparticles provided between the nanofibers, the nanofiber-nanoparticle composite sensing material had an increased response speed and was more stably reacted with the hydrogen sulfide gas at 300° C. Further, due to the presence of the pores formed between the nanofibers, the nanofiber-nanoparticle composite sensing material had a relatively open structure and increased sensitivity, when compared to the sensor with only the nanoparticles.

Figure 13:
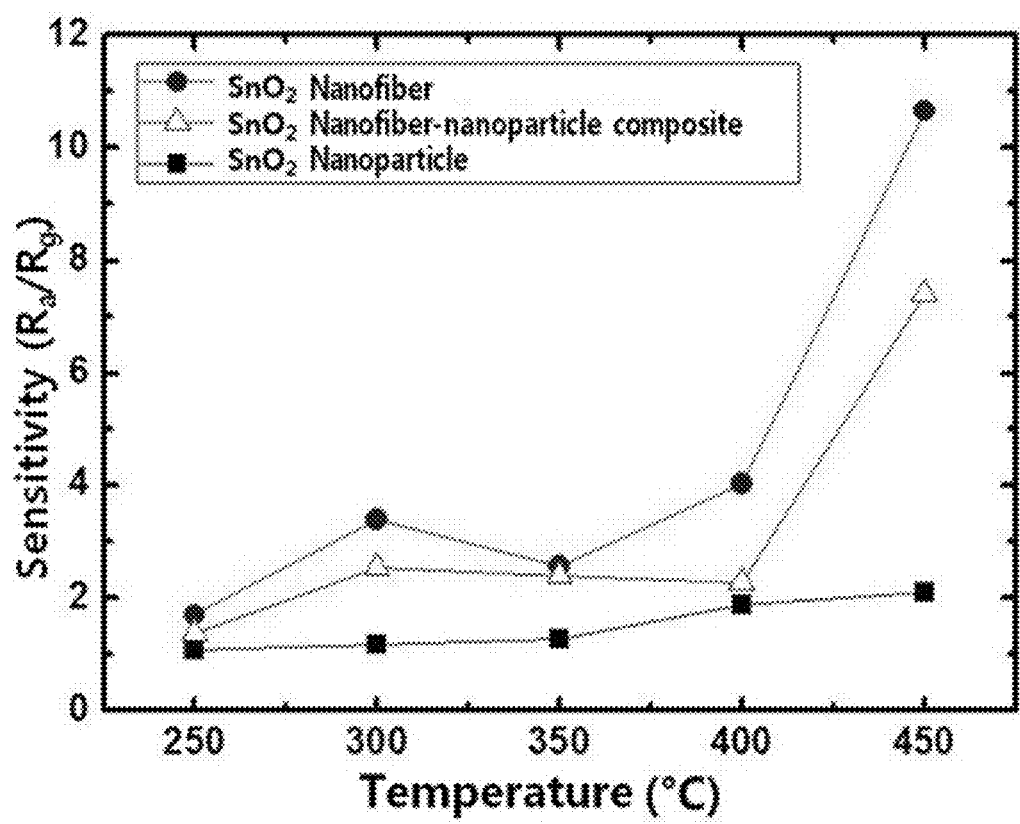
FIG. 13 is a graph showing reactivity characteristics of gas sensors for toluene gas over a temperature range from 250° C. to 450° C. Here, sensing materials of the gas sensors were the tin oxide nanofibers, the tin oxide nanoparticles, and the composite including the tin oxide nanofibers and the tin oxide nanoparticles, according to the first and second embodiments.

FIG. 13 is a graph showing reactivity characteristics of gas sensors for toluene gas over a temperature range from 250° C. to 450° C. Here, sensing materials of the gas sensors were the tin oxide nanofibers, the tin oxide nanoparticles, and the tin oxide nanofiber-nanoparticle composite, according to the first and second embodiments. Similar to the sensitivity for the acetone gas illustrated in FIG. 12, when the gas sensors were exposed to the toluene gas in a temperature range from 250 to 450° C., the sensitivity the gas sensor was the highest in a case of having only the nanofibers and was the lowest in another case of having only the nanoparticles. This shows that the nanofiber-based sensor had the most superior reaction sensitivity. For the case of the nanofiber-nanoparticle composite, the sensitivity of the gas sensor was between those of the other two cases and was slightly smaller than that of the sensor having only the nanofibers. When compared with the result of FIG. 12, the tin oxide nanofiber-nanoparticle composite sensing material had a low sensitivity of 2.141 for 3 ppm toluene gas, as described with respect to the sensitivity at 300° C., while, under the same conditions of temperature and concentration, the tin oxide nanofiber-nanoparticle composite sensing material had a relatively high sensitivity of 13.253 for hydrogen sulfide gas. This shows that the tin oxide nanofiber-nanoparticle composite can be used as a sensing material for selectively detecting the presence of the hydrogen sulfide.

Figure 14:
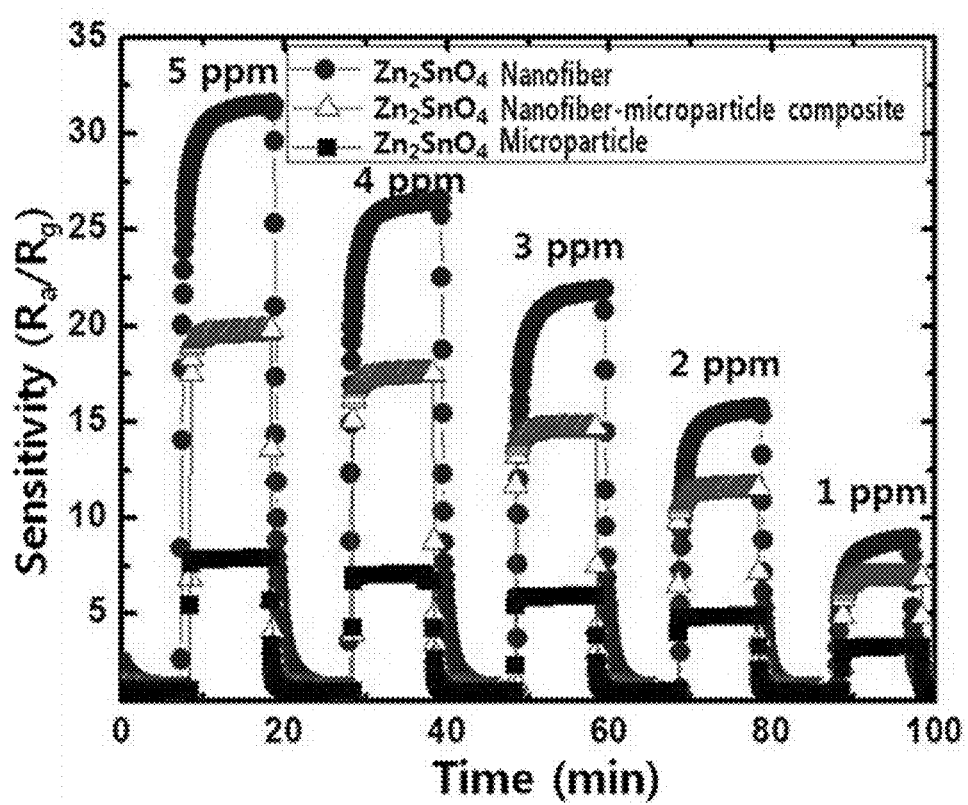
FIG. 14 is a graph showing response characteristics of gas sensors for acetone gas at 450° C. Here, sensing materials of the gas sensors were the zinc stannate nanofibers, the zinc stannate microparticles, and the composite including the zinc stannate nanofibers and the zinc stannate microparticles, according to the third, fourth, and fifth embodiments.

FIG. 14 is a graph showing reactivity characteristics of gas sensors for acetone gas at 450° C. Here, sensing materials of the gas sensors were zinc stannate sensing materials (for example, zinc stannate nanofibers, zinc stannate microparticles, and a composite of zinc stannate nanofibers and zinc stannate microparticles) according to the third, fourth, and fifth embodiments. The gas response $R_a/R_g$ of the gas sensor for acetone gas was measured at 450° C., when a concentration of acetone was changed from 5 ppm to 1 ppm by 1 ppm. As shown in FIG. 14, the sensor using the zinc stannate nanofiber sensing material had the highest sensitivity, $R_a/R_g$, of about 31.526 for 5 ppm acetone, similar to the result of FIG. 12 for the tin oxide-based gas sensor. By contrast, the sensor using the zinc stannate microparticle sensing material had a sensitivity of about 7.906 for 5 ppm acetone, which was at least four times lower than that of the nanofiber sensor. This is because the nanofiber sensor has a large specific surface area and a porous structure allowing for rapid diffusion and permeation of a gas. Here, the microparticle sensor had fast response and recovery speeds. The response speed may be defined to be a response time required to reach 90% of the highest resistance, and the graph shows that saturation of the microparticle sensor occurred very quickly after injection of the acetone gas. The zinc stannate nanofiber-microparticle composite sensor had a relatively high sensitivity of 19.786, for 5 ppm acetone, and the fast response and recovery speeds. In other words, the sensitivity of the nanofiber-microparticle composite was lower than that of the nanofiber sensor but was higher than that of the microparticle sensor, and moreover, the nanofiber-microparticle composite had a stable reaction property.

The following Table 1 shows sensitivity, response time, and recovery time characteristics of the gas sensors using zinc stannate sensing materials (for example, the nanofibers, the microparticles, and the nanofiber-microparticle composite) according to the third, fourth, and fifth embodiments. In the experiment, the gas sensors were exposed to 5 ppm acetone gas.

TABLE 1

|  | zinc stannate nanofiber sensor | zinc stannate nanofiber-microparticle composite sensor | zinc stannate microparticle sensor |
|---|---|---|---|
| Sensitivity (gas response) @ 5 ppm | 31.5 | 19.8 | 7.9 |
| Response time (sec) | 80.0 | 10.0 | 6.0 |
| Recovery time (sec) | 99.2 | 34.0 | 29.6 |

Table 1 shows sensitivities, response speeds, and recovery speeds of the zinc stannate nanofiber, zinc stannate microparticle, and zinc stannate nanofiber-microparticle composite sensors manufactured according to the second embodiment and exposed to 5 ppm acetone. As illustrated in the graph of FIG. 14, for the nanofiber-microparticle composite sensor, the sensitivity thereof was slightly lower than that of the nanofiber sensor, but the response and recovery times thereof were 10 sec and 34 sec, respectively. That is, the nanofiber-microparticle composite sensor had about eight times faster response time and about three times faster recovery time, when compared with the nanofiber sensor having the response and recovery times of 80 sec and 99.2 sec. Further, the nanofiber-microparticle composite sensor had about 2.5 times higher sensitivity of 19.786, when compared with the microparticle sensor having the sensitivity of 7.906. From Table 1, it can be said that the use of the nanofiber-microparticle composite allows the sensor to have a high sensitivity, which is slightly lower than the nanofiber-based sensor but is sufficiently high, and moreover to react with a gas in a more stable and exact manner. Especially, due to thermal and structural stabilities of the nanofiber-microparticle composite thermal stability, the use of the nanofiber-microparticle composite allows the sensor to have an increased lifetime.

In the previous embodiments, tin oxide ($SnO_2$) and zinc stannate ($Zn_2SnO_4$) were exemplarily described as the metal oxide for the sensing materials. However, any metal oxide semiconductor material can be used for the sensing material, if it can be manufactured using an electrospinning method and provided in the form of nanoparticles or microparticles. For example, in certain embodiments, the sensing material may be formed of or include at least one selected from the group consisting of $SnO_2$, $ZnO$, $TiO_2$, $In_2O_3$, $Zn_2SnO_4$, $WO_3$, $Co_3O_4$, $NiO$, $V_2O_5$, and $CuO$ and may be provided in the form of nanofibers, microparticles, or a composite of nanofibers and microparticles. Further, graphene or a nanoparticle catalyst, which may be formed of or include at least one selected from the group consisting of Pt, Pd, Ag, Au, $IrO_2$, $RuO_2$, and $Rh_2O_3$ may be used to improve functions or characteristics (e.g., sensitivity, selectivity, or base resistance stability) of the composite sensing material containing polycrystalline nanofibers, microparticles, and nanoparticles.

The afore-described sensors (e.g., the metal oxide nanofiber-microparticle-nanoparticle composite-based sensor) may be used to detect various gaseous materials such as typical harmful gases (e.g., CO, $NO_R$, and $SO_X$), the sick-house-syndrome-causing materials (e.g., xylene, benzene, and formaldehyde (HCHO)), the radioactivity materials (e.g., radon) in rock, soil, or building materials, or the colorless water-soluble toxic gases (e.g., hydrogen cyanide (HCN)), in addition to the previously-described hydrogen sulfide, toluene, and acetone gases. Further, the afore-described sensors may be used to diagnose a variety of diseases; for example, they can be used to detect biomarkers (e.g., $H_2S$, ethanol, NO, $NH_3$, isoprene, toluene, acetone, and so forth) contained in the exhalation gas.

According to example embodiments, a sensing material for a gas sensor may include a composite with at least three different morphologies of metal oxide semiconductor material: for example, nanofibers, microparticles, and nanoparticles. Accordingly, the sensing material may have a specific surface area larger than that of a microparticle-based sensing material. Further, by using the composite-based sensing material, it is possible to overcome structural, thermal, and electrical issues, which may occur in a nanoparticle-based sensing material. For example, the use of the composite-based sensing material allows the gas sensor to have long lifetime reliability and a low base resistance, and moreover, to stably measure a change in electric resistance, which may occur when a gas is detected. Especially, the polycrystalline nanofibers, the microparticles, and the nanoparticles in the composite may be contained in a composition ratio of X:Y:Z, respectively, where X ranges from 20 to 95 wt %, Y ranges from 0 to 80 wt %, Z ranges from 0 to 30 wt %, and X+Y+Z=100 wt %. In the sensor or a sensor array therewith, the composition ratio between the polycrystalline nanofibers, the microparticles, and the nanoparticles may be freely changed to improve a sensing selectivity for several gases, under the above condition.

While example embodiments of the inventive concepts have been particularly shown and described, it will be understood by one of ordinary skill in the art that variations in form and detail may be made therein without departing from the spirit and scope of the attached claims.

What is claimed is:

1. A composite sensing material comprising:
   a composite containing polycrystalline nanofibers formed of a metal oxide and at least one of microparticles and nanoparticles formed of a same metal oxide,
   wherein the polycrystalline nanofibers, the microparticles, and the nanoparticles have weight percentages X, Y, and Z, respectively, whose sum is 100 wt %, and the composite has:
   a composition ratio of X:Y:Z for the composite containing the polycrystalline nanofibers, the microparticles, and the nanoparticles, where the value X is greater than or equal to 20 wt % and is smaller than or equal to 95 wt %, the value Y is greater than 0 wt % and is smaller than or equal to 80 wt %, and the value Z is greater than 0 wt % and is smaller than or equal to 30 wt %,
   a composition ratio of X:Y, for the composite containing the polycrystalline nanofibers and the microparticles, or of X:Z, for the composite containing the polycrystalline nanofibers and the nanoparticles, where the value X is greater than or equal to 10 wt % and is smaller than or equal to 90 wt %, the value Y or Z is greater than or equal to 10 wt % and is smaller than or equal to 90 wt %.

2. The composite sensing material of claim 1, wherein the microparticle or the nanoparticle are disposed to partially fill pores between the polycrystalline nanofibers and are attached to the polycrystalline nanofibers, such that the composite sensing material has a more compact structure than a sensing material having only the polycrystalline nanofibers.

3. The composite sensing material of claim 1, wherein the metal oxide for the polycrystalline nanofibers or the metal oxide for the microparticles and the nanoparticles comprises one material or a composite containing at least two materials selected from the group consisting of $SnO_2$, $ZnO$, $TiO_2$, $In_2O_3$, $Zn_2SnO_4$, $WO_3$, $Co_3O_4$, $NiO$, $V_2O_5$, and $CuO$.

4. The composite sensing material of claim 1, wherein the polycrystalline nanofibers have a diameter range from 100 nm to 1 μm and an aspect ratio range from 2 to 5000,
   the microparticles have a size range from 200 nm to 3 μm, and
   the nanoparticles have a size range from 10 nm to 100 nm.

5. The composite sensing material of claim 1, wherein the composite containing the polycrystalline nanofibers, the microparticles, and the nanoparticles comprises:
   large-sized pores formed between the polycrystalline nanofibers to have a size ranging from several hundreds of nanometers to several tens of micrometers;
   pores formed between the microparticles to have a size ranging from several tens of micrometers to several micrometers; and
   small-sized pores formed between the nanoparticles to have a size smaller than or equal to 100 nanometers.

6. The composite sensing material of claim 1, wherein the composite further comprises at least one catalyst particle, which is formed of Pt, Pd, Ag, Au, $IrO_2$, $RuO_2$, or $Rh_2O_3$, has a size range from 1 nm to 10 nm, and has a weight percent of 0.01-5 wt % in the composite.

7. The composite sensing material of claim 1, wherein the composite further comprises at least one graphene, which is formed of non-oxidized graphene, oxidized graphene, reduced graphene oxide, or thin graphite and has a weight percent of 0.01-2 wt % in the composite.

8. The composite sensing material of claim 1, wherein the composite further comprises at least one catalyst particle, which is formed of Pt, Pd, Ag, Au, $IrO_2$, $RuO_2$, or $Rh_2O_3$, has a size range from 1 nm to 10 nm, and has a weight percent of 0.01-5 wt % in the composite, and at least one graphene, which is formed of non-oxidized graphene, oxidized graphene, reduced graphene oxide, thin graphite and has a weight percent of 0.01-2 wt % in the composite.

9. A gas sensor with the composite sensing material according to claim 1.

10. A sensor array comprising the gas sensor of claim 9.

11. A method of manufacturing a composite sensor, comprising:
- (a) sequentially performing an electrospinning process and a thermal treatment process to synthesize polycrystalline nanofibers made of metal oxide, the electrospinning process being performed using a polymer-containing solution, in which a precursor salt is contained, the thermal treatment process being performed to form the metal oxide from the precursor salt;
- (b) synthesizing metal oxide microparticles using a solid state reaction;
- (c) synthesizing metal oxide nanoparticles;
- (d) mixing the polycrystalline nanofibers, the microparticles, and the nanoparticles to synthesize a composite-containing solution having a composition ratio of X:Y:Z, whose sum is 100 wt %, and values X, Y, and Z are weight percentages of the polycrystalline nanofibers, the microparticles, and the nanoparticles, the value X is greater than or equal to 20 wt % and is smaller than or equal to 95 wt %, the value Y is greater than 0 wt % and is smaller than or equal to 80 wt %, and the value Z is greater than 0 wt % and is smaller than or equal to 30 wt %;
- (e) coating a sensor electrode with the composite-containing solution; and
- (f) thermally treating the sensor electrode.

12. The method of claim 11, wherein the step (e) further comprises adding nanoparticle catalyst into the composite-containing solution, before the coating, and the nanoparticle catalyst comprises at least one selected from the group consisting of Pt, Pd, Ag, Au, $IrO_2$, $RuO_2$, and $Rh_2O_3$.

13. The method of claim 11, wherein the step (e) further comprises adding a graphene-containing solution into the composite-containing solution, before the coating.

14. The method of claim 11, wherein the step (e) further comprises adding a nanoparticle-catalyst-containing solution and a graphene-containing solution into the composite-containing solution, before the coating.

15. The method of claim 11, wherein at least one of the polycrystalline nanofibers, the microparticles, and the nanoparticles comprises one material or a composite containing at least two materials selected from the group consisting of $SnO_2$, ZnO, $TiO_2$, $In_2O_3$, $Zn_2SnO_4$, $WO_3$, $Co_3O_4$, NiO, $V_2O_5$, and CuO.

16. The method of claim 11, wherein the step (e) is performed using at least one of screen-printing, drop-coating, spin-coating, inkjet-printing, electro-hydrodynamic deposition (EHD), and dispensing processes.

17. The method of claim 11, further comprising a step (g) of manufacturing at least two composite sensors of different types to manufacture a sensor array.

18. The method of claim 17, wherein the step (g) is performed in such a way that the sensor array comprises 2-30 sensors that are different from each other in terms of at least one of 1) a type of the metal oxide for at least one of the polycrystalline nanofibers, the microparticles, and the nanoparticles, 2) a composition ratio of the polycrystalline nanofibers, the microparticles, and the nanoparticles, 3) a kind of nanoparticle catalyst contained in the composite-containing solution, and 4) a kind of graphene contained in the composite-containing solution.

* * * * *